US008153366B2

(12) United States Patent
Rieder et al.

(10) Patent No.: US 8,153,366 B2
(45) Date of Patent: Apr. 10, 2012

(54) METHODS AND COMPOSITIONS FOR PREDICTING DRUG RESPONSES

(75) Inventors: Mark J. Rieder, Seattle, WA (US); Allan Rettie, Langley, WA (US)

(73) Assignee: University of Washington, Seattle, WA (US)

( * ) Notice: Subject to any disclaimer, the term of this patent is extended or adjusted under 35 U.S.C. 154(b) by 1233 days.

(21) Appl. No.: 11/687,153

(22) Filed: Mar. 16, 2007

(65) Prior Publication Data
US 2008/0057500 A1 Mar. 6, 2008

Related U.S. Application Data

(62) Division of application No. 10/967,879, filed on Oct. 18, 2004, now Pat. No. 7,445,896.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...... 435/6.1; 435/6.11; 435/91.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 5,547,835 A | 8/1996 | Koster | |
| 6,043,031 A | 3/2000 | Koster et al. | |
| 2006/0166239 A1 | 7/2006 | Chen et al. | |
| 2009/0215045 A1 | 8/2009 | Stafford et al. | |

FOREIGN PATENT DOCUMENTS

| | | |
|---|---|---|
| WO | WO 95/34679 | 12/1995 |
| WO | WO 2005/030039 | 4/2005 |
| WO | WO 2005/040367 | 5/2005 |
| WO | 2006/044686 | 4/2006 |

OTHER PUBLICATIONS

Lucentini (The Scientist; 2004, vol. 24, p. 20).*
Hegele (Arterioscler. Thromb. Vasc. Biol.; 2002, vol. 22, pp. 156-1061).*
Wu et al; Pharmacogenomics, vol. 9, pp. 1-9, 2008.*
NCBI Accession No. AY587020, Rieder et al., (May 14, 2004).
Internet website, http://pga.gs.washington.edu/data/vkorc1/, posted to the internet on Mar. 31, 2004 (8 pages).
Rieder et al., "Effect of VKORC1 Haplotypes on Transcriptional Regulation and Warfarin Dose," *New England Journal of Medicine* 352:2285-2293 (2005).
Wadelius et al., "Common VKORC1 and GGCX Plymorphisms Associated with Warfarin Dose," *Pharmacogenomics Journal* 5:262-270 (2005).
Geisen et al., "VKORC1 Haplotypes and Their Impact on the Inter-individual and Inter-ethnical Variability of Oral Anticoagulation," *Thrombosis and Haemostasis* 94:773-770 (2005).
Harrington et al., "Pharmacodynamic Resistance to Warfarin Associated with a Val66Met Substitution in Vitamin K Epoxide Reductase Complex Subunit 1," *Thrombosis and Haemostastis* 93:23-26 (2005).

(Continued)

*Primary Examiner* — Jehanne Sitton
(74) *Attorney, Agent, or Firm* — Nixon Peabody LLP

(57) ABSTRACT

The present invention relates to methods and compositions for predicting drug responses. In particular, the present invention provides methods and compositions for determining individualized Warfarin dosages based on genotype of DNA polymorphisms and haplotypes derived from them in the VKORC1 gene.

17 Claims, 6 Drawing Sheets

OTHER PUBLICATIONS

Devlin and Risch, 29(2):311-22 (1995).
Fang et al., *Arch Intern Med* 164:55-60 (2004).
Gage et al., *Stroke* 31:822-7 (2000).
Higashi et al., *Jama* 287:1690-8 (2002).
Rost et al., *Nature* 427:537-41 (2004).
Gate et al., *Thromb Haemost* 91:87-94 (2004).
Suttie, *Adv Exp Med Biol* 214:3-16 (1987).
Li et al., *Nature* 427:541-4 (2004).
Fasco et al., *Biochemistry* 22:5655-60 (1983).
Lesko et al., *Nat Rev Drug Discov* 3:763-9 (2004).
Aithal et al., *Lancet* 353:717-9 (1999).
Rettie et al., *Epilepsy Res* 35:253-5 (1999).
Blann et al., *Br J Haematol* 107:207-9 (1999).
Gan et al., *Int J Hematol* 78:84-6 (2003).
Yu et al., Qjm 89:127-35 (1996).
Chenhsu et al., *Ann Pharmacother* 34:1395-401 (2000).
Absher et al., *Ann Pharmacother* 36:1512-7 (2002).
Przeworski et al., *Trends Genet* 16:296-302 (2000).
Crawford et al., *Am J Hum Genet* 74:610-22 (2004).
Drysdale et al., *Proc Natl Acad Sci USA* 97:10483-8 (2000).
Durrin et al., "Vitamin D Receptor 3'-untranslated Region Polymorphisms: Lack of Effect on mRNA Stability," *Biochim Biophys Acta* 1453:311-20 (1999).
Carter et al., "Prothrombin G20210A is a Bifunctional Gene Polymorphism," *Thromb Haemost* 87:846-53 (2002).
D'Andrea Giovanna et al., "A Polymorphism in the VKORC1 Gene is Associated with an Interindividual Variability in the Dose-Anticoagulant Effect in Warfarin," *Blood* 105(2):64.
Rost et al., "Mutations in VKORC1 Cause Warfarin Resistance and Multiple Coagulation Factor Deficienty Tupe 2," *Nature* 427(6974):537-41 (2004).
Alignment for Genbank Accession No. AC135050 (Feb. 2003).
Alignment for Genbank Accession No. AY58020 (May 2004).
Toomajian et al., *Genetics* 161:1609-1623 (2002).
ss21323934 (dbSNP database assay ID for rs9934438 (Mar. 19, 2004).
ss13773513 (dbSNP database assay ID for rs9934438 (Nov. 5, 2003).
ss19348150 (dbSNP database assay ID for rs9934438 (Feb. 20, 2004).
Ss24683640 (dbSNP database assay ID for rs9934438 (Aug. 21, 2004).
Hegele (Arterioscler. Thromb. Vasc. Biol.; 22:1056-1061, 2002).
Lucentini (The Scientist; 24:20, 2004).
Wu et al. (Pharmacogenomics 9:1-9, 2008).

* cited by examiner

Figure 2
SEQ ID NO: 1

```
   1  cagaggacaa catagatagg ttcggagact actcagagaa agggagagag aatgctaggt
  61  tatctttcag ctgttttagc tgcttattgt tccagcttta gccaccatct gactgcaatt
 121  gtatgagcca gaaatagcca ggtaaaattg tcttcccaaa ttcctagtgc acaaaaactg
 181  tcagaggctg gggcagtgg ctcactcctg taatcccagc agcactttgg gaagccaggg
 241  tgggagaact gcttgagccc aggagttaga ggcaacataa caacaactca tctctaatga
 301  aaaaaaaaaa aaaagaaaga aaaggccag gcacagtggc tcacgcctgt aatcccagca
 361  ctttaggaag ccaaggaggg tggatcatga ggtcaggagt ttgagaccag cctggccaat
 421  atggtgaaac cccgtctcta ctaaaaacac aaaaatcagc cacgcatagt ggctggtgcc
 481  tgtaatcaca gctactcagg aggctaaggc aggagaatca cttgaatccg ggaggcagag
 541  gttgcagtga gccgagattg caccactgca tttcagcctg ggcagcagag tgggactgtc
 601  tcacattaat taattaattg attaaatgct agaagaaaat atggtcaaaa tcttttataa
 661  ctcttggagt gaggaaggca atctcggctc actacaactt ccacctcccg ggttcaaatg
 721  attctcctgc ctcagcctcc tgagtagctg ggattacagg cacccaccac catgcccggc
 781  taattttgt attttagta gagacgaggt ttcgccatgt tggccaagct tgtcttaaac
 841  tcctgacctc aggtgatcca cccacctcag cctcccaaat tgctgggatt acaggcatga
 901  gccaccatgc ccgcctaat tttaaaaatg tttataaaga cagagtctta ccacgttgtc
 961  cagacctgtc tcaaactcct gggctcaagt cattgtcttg tctcagcctc ccaaagttct
1021  gggactacag gtgtgcacca ccacacctgg ctaattttgt ttatttttta tagagtgagg
1081  gtctccctgt gttgtccagg gtgtctcaaa ctcctgggct caagtggtcc tctgcctca
1141  gcctcccaaa gtgctgggat tataggcata agccactgca cctggcccca gtgtgtgtct
1201  tctgaggcta agtcataaag agattgcggc ttctattttg cttcctctta gatcactcat
1261  tctggggaa accaacaata aataacagga acacaccagg agatcagaga aagctgagat
1321  acaggcctaa tgccagtcc tctgtattca tttctaattg ctgctgtaac aagttactgc
1381  acatttaatg atgtaaaaca acacaaattt atcttacagt tctgtagctt agaagtctga
1441  cagagtctca ctgggctgaa atcaagatgt tgatagttcc ttcccggtga ctctagagtg
1501  agaatccagt tcttacccct ttcttgcctt tagaggccac ccgtatttat tagctcacaa
1561  tcccttcct ccatcttcaa accagaaaca ttgcagctct ctgtgtcttt ttctttact
1621  cacatctccc tctgactttc ttctgccatc ctccttcatt ttttaaggac ccctgtgggc
1681  caggcatggt ggcttatgcc tgtaatccca gcactttgag aggcggaggc aggcgggtca
1741  cctgaggtca ggagttccag accagcctgg ccaacatggc aaaacccat ctccactgaa
1801  aatacaaaaa ttgggccagg cacggcggct cacaccgta atcccatac tttgagaggc
1861  tgaggcaggt ggatcacttg aggtcaggag ttcaagacca gcctggccaa catggtgaaa
1921  tcccgtctct actaaaaaaa aaaaaatta caataattag tcaggcgtgg tggccagcac
1981  ctataatccc agctacttgg gaggttgagg cacaagaatt gcttgaaccc gagaggggga
2041  ggttgcagtg agctgagatt gcaccaccgt actccagcct ggatgacaga gcaagactct
2101  gtctcaaaat aaaaattaag ataaataata aaaataaat aaaaatcagc aaattaggcc
2161  aggtgtggtg gtggctcatg cctgtactcc agcactttg aggtggaag ttgcttgaa
2221  accagaagtt tagaccagcc tgggaaacaa agtgagaccc catctctaca aaataaaaa
2281  taaattagcc aggtgtggtg ggacgtactt gtactcctag ctactaggga ggctgaggtg
2341  caagaatcgc ttgaacctgg gagacggagg ttgcagtgag ttatgacagt gccactacac
2401  tccagcctgg gtgtcaaggg tctttgaaaa aataaacaaa ataggctggg cgtggtggct
2461  tacacttgta atcccagcac tttgggaggc tgaggcaggc agatcacaaa gtcaggagtt
2521  cgagaccagc ctggccaaca cagtgaaacc ccgtctctac taaaaataca aaaattagcc
2581  aggcatggtt gcacgcgcct gtagtcccaa ctctcgggga ggctgaggca ggagaatggc
2641  ttgaacctgg ggggggcgg aagttataat gagccaagat tgtgccactg cactccagcc
2701  taggcaacag agcgagactc cgtctcaaaa ataaaataa aataaatca atagagcctg
2761  gtatgatggc tcacgcctat aatcccagca ctttgggagg cccaggtggg tggatcatct
2821  gaggtcagga gtttgagacc agcctgacca acatggagaa accccatctc tactaaaaat
2881  acaaaaatt agccaggcgt ggtggcacat gcctataatc cagctactc aggagcctga
2941  ggcaggagaa tcgcttaac cggggaggtg gaggttgcgg tgagtcgaga tagcaccatt
3001  gcattctagc ctgggcaaca agagcaaaac tccatctcaa aaataaataa ataaatagat
```

Figure 2 (cont)

```
3061 agataggctg ggcacggtgg ctcacgcctg taatcccagc actttgggag gccgaggtgg
3121 gcggatcacc tgaggtcagg agttcaagac cagcctggcc aatatagcga aaccctgtct
3181 ctactaaaaa tttaaaaaat tagccaggca tgatggcggg tgcctgtaat cccagctact
3241 cgggaggctg aggcaggaga atctctcgaa cctggcaggc ggaggttgca gtgagccgag
3301 atcacaccat tgcactccag ttgggcaaca agagcgaaac tccacctcaa aaacaaaata
3361 aaataaaata aaatcaggag attggtcagc ttaattccat ctgcaacctt aattcccttt
3421 tggccattta acctatcata ttcacaagtt ccagggattc atgcagggac atctttggtg
3481 accattattc tgtctaccac actctctaga agagagtaga tgtgagaaac agcatctgga
3541 gagggaggag ccagcaggag agggaaatat cacagacgcc agaggaagag agttcccaga
3601 agggtaggtg caacagtaag ggatccctct gggaagtcaa gcaagagaag acctgaaaaa
3661 caaccattgg ccgggtgcgg tggctcacgc ctataatcct agcattttgg gaggccgagg
3721 tgggtggatc acttgaggtc aggagtttaa gacaagcctg gccaacatgg tgaaaccctg
3781 tctctactaa aaatacaaaa attagccaga catggtggca ggcacctgta gtccaaacta
3841 cttgggaggc tgaggcacga gaaccacttg aaccctggag gcggaagttg cagtgagccg
3901 agatggcacc gctgcactcc agcctgggcg acagagtgag actccgtctc aaaataagta
3961 aataaataaa taaataaacca ttgggtctag cgtcttggtg acaccagcca ctaggtgtca
4021 gggcaatgct ggaggcagca gctagtttat ggcgtgggca gcaaggaaga agtgaggaag
4081 tagagactgg gagtgtagaa tctttccaaa aacttgaatg tggaggggta gatgggataa
4141 tgccgggaga ggaggctggt gaaggacctc ttagtgaagg gagatttgtt gctgtttctg
4201 agatgggaaa gagaaacaag ttgcagtgta gatggggagg atggagaggt tgaaggtgta
4261 ggagaggtga gtcaccatca gatgggcgt ctgtgaagga gagacctcat ctggcccaca
4321 gcttggaaag gagagactga ctgttgagtt gatgcaagct caggtgttgc caggcgggcg
4381 ccatgatagt agagaggtta ggatactgtc aagggtgtgt gtggccaaag gagtggttct
4441 gtgaatgtat gggagaaagg gagaccgacc accaggaagc actggtgagg caggacccgg
4501 gaggatggga ggctgcagcc cgaatggtgc ctgaaatagt ttcaggggaa atgcttggtt
4561 cccgaatcgg atcgccgtat tcgctggatc ccctgatccg ctggtctcta ggtcccggat
4621 gctgcaattc ttacaacagg acttggtgg gggtaagcgc aaatgctgtt aaccacacta
4681 acacactttt tttttttctttt tttttttttg agacagagtc tcactctgtc ggcctggctg
4741 gagtgcagtg gcacgatctc ggctcactgc aacctccggc tccccggctc aagcaattct
4801 cctgcctcag cctcccgagt agctgggatt acaggcatgt gccaccacgc ccggctaatt
4861 tttgtatttt tagttgagat ggggtttcac catgttggcg aggctggtct tgaactcctg
4921 acctcaggta atccgccagc ctcggcctcc caaagtgctg ggattacaag cgtgagccac
4981 cgtgcccggc caacagtttt taaatctgtg gagacttcat ttcccttgag gccttgcagc
5041 cgcgccgact acaactccca tcatgcctgg cagccgctgg ggccgcgatt ccgcacgtcc
5101 cttacccgct tcactagtcc cggcattctt cgctgttttc ctaactcgcc cgcttgacta
5161 gcgccctgga acagccattt gggtcgtgga gtgcgagcac ggccggccaa tcgccgagtc
5221 agagggccag gaggggcgcg gccattcgcc gcccggcccc tgctccgtgg ctggtttttct
5281 ccgcggcgcg ctcggcgga acctggagat aatgggcagc acctggggga gccctggctg
5341 ggtgcggctc gctctttgcc tgacgggctt agtgctctcg ctctacgcgc tgcacgtgaa
5401 ggcggcgcgc gcccgggacc gggattaccg cgcgctctgc gacgtgggca ccgccatcag
5461 ctgttcgcgc gtcttctcct ccaggtgtgc acgggagtgg gaggcgtggg gcctcggagc
5521 agggcggcca ggatgccaga tgattattct ggagtctggg atcggtgtgc ccggggaacg
5581 gacacggggc tggactgctc gcggggtcgt tgcacagggg ctgagctacc cagcgatact
5641 ggtgttcgaa ataagagtgc gaggcaaggg accagacagt gctggggact gggattattc
5701 cggggactcg cacgtgaatt ggatgccaag gaataacggt gaccaggaaa ggcggggagg
5761 caggatggcg gtagagattg acgatggtct caaggacggc gcgcaggtga aggggggtgt
5821 tggcgatggc tgcgcccagg aacaaggtgg cccggtctgg ctgtgcgtga tggccaggcg
5881 ttagcataat gacggaatac agaggaggcg agtgagtggc cagggagctg gagattctgg
5941 ggtccagggc aaagataatc tgcccccgac tccagtctc tgatgcaaaa ccgagtgaac
6001 cgttatacca gccttgccat tttaagaatt acttaagggc cgggcgcggt ggcccactcc
6061 tgtaatccca gcactttggg aggccgagtc ggatggatca cttgaagtca ggagttgacc
6121 agcctggcca acatggtgaa agcctgtctc taccaaaaat agaaaaatta atcgggcgct
6181 atggcgggtg ccttaatccc agctactcgg ggggctaag gcaggagaat cgcttgaacc
6241 cgggaggcgg aggtttcagt gagccgagat cgcgccactg cactccagcc tgggccagag
6301 tgagactccg tctcaaaaaa aaaaaaaaaa aaaaaaaaa agagacttac ttaaggtcta
6361 agatgaaaag cagggcctac ggagtagcca cgtccgggcc tggtctgggg agaggggagg
6421 ataggttcag tgacatggaa tcctgacgtg gccaaaggtg cccggtgcca ggagatcatc
```

Figure 2 (cont)

```
6481 gaccettgga ctaggatggg aggtcgggga acagaggata gcccaggtgg cttcttggaa
6541 atcacctttc tcgggcaggg tccaaggcac tgggttgaca gtcctaacct ggttccaccc
6601 caccccaccc ctctgccagg tggggcaggg gtttcgggct ggtggagcat gtgctgggac
6661 aggacagcat cctcaatcaa tccaacagca tattcggttg catcttctac acactacagc
6721 tattgttagg tgagtggctc cgccccctcc ctgcccgccc cgcccgccc ctcatccccc
6781 ttggtcagct cagccccact ccatgcaatc ttggtgatcc acacagctga cagccagcta
6841 gctgctcatc acggagcgtc ctgcgggtgg ggatgtgggg aggtaactaa caggagtctt
6901 ttaattggtt taagtactgt tagaggctga agggccctta aagacatcct aggtccccag
6961 gtttttttgtt tgttgttgtt ttgagacagg gtctggctct gttgcccaaa gtgaggtcta
7021 ggatgcccct agtgtgcact ggcgtgatct cagttcatgg caacctctgc ctccctgccc
7081 aagggatcct cccaccttag cctcccaagc agctggaatc acaggcgtgc accactatgc
7141 ccagctaatt tttgtttttg ttttttttttg gtagagatgg tgtctcgcca tgttgcccag
7201 gctggtctca agcaatctgt ctgcctcagc ctccaaagt gctgggggga ttacaggcgt
7261 gagctaccat gccccaccaa cacccagtt ttgtggaaaa gatgccgaaa ttcctttta
7321 aggagaagct gagcatgagc tatcttttgt ctcatttagt gctcagcagg aaaatttgta
7381 tctagtccca taagaacaga gagaggaacc aagggagtgg aagacgatgg cgccccaggc
7441 cttgctgatg ccatatgccg gagatgagac tatccattac caccottccc agcaggctcc
7501 cacgctccct ttgagtcacc cttcccagct ccagagaagg catcactgag ggaggcccag
7561 caccacggtc ctggctgaca catggttcag acttggccga tttatttaag aaattttatt
7621 gctcagaact ttccctccct gggcaatggc aagagcttca gagaccagtc ccttggaggg
7681 gacctgttga agccttcttt ttttttttt ttaagaaata atcttgctct gttgcccagg
7741 ctggagtgca gtggcacaat catagctcac tgtaacctgg ctcaagcgat cctcctgagt
7801 agctaggact ataggcatgt cactgcaccc agctaatttt ttttttttttt ttttttttt
7861 ttttgcgaca tagtctcgct ctgtcaccag gctggagtgc agtggcacga tcttggctca
7921 ctgcaacctc tgcctcccgg gttcaagcaa ttttcctgcc tcagcctcct gagtagctgg
7981 gactacaggc gcgtgtcacc acgcccagct aattttgta ttttagtgg agacagggtt
8041 tcaccatgtt ggctaggatg gtctcaatct cttgacctgg tgatccatcc gccttggcct
8101 cccaaagtgc taggattaca ggcgtgagtc aacctcaccg ggcattttt ttttgagacg
8161 aagtcttgct cttgctgccc aagctggaat gtggtggcat gatctcggct cactgcaacc
8221 tccacctcct aggttcaagc gattctccac cttagcctcc ccagcagctg ggattacagg
8281 tgcccatcaa cacacccggc taatttttgt attttatta gagatggggt tttgccatgt
8341 tggccagget gtctctcgaac tcctaacctc aggtgatcca ccccattgg cctcccaaaa
8401 tactgggatt acaggcatga gccaccgtgc ccagctgaat ttctaaattt ttgatagaga
8461 tcgggtcttt ctatgttgcc caagctggtc ttgaactcct agcctaaagc agtcttccca
8521 cctcggcctc ccagagtgtt tggaatacgt gcgtaagcca ccacatctgc cctggagcct
8581 cttgttttag agacccttcc cagcagctcc tggcatctag gtagtgcagt gacatcatgg
8641 agtgttcggg aggtggccag tgcctgaagc ccacaccgga ccctcttctg ccttgcaggt
8701 tgcctgcgga cacgctgggc ctctgtcctg atgctgctga gctccctggt gtctctcgct
8761 ggttctgtct acctggcctg gatcctgttc ttcgtgctct atgatttctg cattgtttgt
8821 atcaccacct atgctatcaa cgtgagcctg atgtggctca gtttccggaa ggtccaagaa
8881 ccccagggca aggctaagag gcactgagcc ctcaacccaa gccaggctga cctcatctgc
8941 tttgctttgg catgtgagcc ttgcctaagg gggcatatct gggtccctag aaggccctag
9001 atgtggggct tctagattac ccctcctcc tgccatcccc gcacatgaca atggaccaaa
9061 tgtgccacac gctcgctctt ttttacaccc agtgcctctg actctgtccc catgggctgg
9121 tctccaaagc tctttccatt gcccagggag ggaaggttct gagcaataaa gtttcttaga
```

Figure 2 (cont)

```
    9181 tcaatcagcc aagtctgaac catgtgtctg ccatggactg tggtgctggg
cctccctcgg
    9241 tgttgccttc tctggagctg ggaagggtga gtcagaggga gagtggaggg
cctgctggga
    9301 agggtggtta tgggtagtct catctccagt gtgtggagtc agcaaggcct
ggggcaccat
    9361 tggccccac cccaggaaa caggctggca gctgctcct gctgcccaca
ggagccaggc
    9421 ctcctctcct gggaaggctg agcacacacc tggaagggca ggctgccctt
ctggttctgt
    9481 aaatgcttgc tgggaagttc ttccttgagt ttaactttaa ccctccagt
tgccttatcg
    9541 accattccaa gccagtattg gtagccttgg agggtcaggg ccaggttgtg
aaggtttttg
    9601 ttttgcctat tatgccctga ccacttacct acatgccaag cactgtttaa
gaacttgtgt
    9661 tggcagggtg cagtggctca cacctgtaat ccctgtactt gggaggcca
aggcaggagg
    9721 atcacttgag gccaggagtt ccagaccagc ctgggcaaaa tagtgagacc
cctgtctcta
    9781 caaaaaaaaa aaaaaaaaa aattagccag gcatggtggt gtatgtacct
atagtcccaa
    9841 ctaatcggga agctggcggg aagactgctt gagcccagaa ggttgaggct
gcagtgagcc
    9901 atgatcactg cactccagcc tgagcaacag agcaagaccg tctccaaaaa
aaaacaaaaa
    9961 acaaaaaaaa acttgtgtta acgtgttaaa ctcgtttaat ctttacagtg
atttatgagg
   10021 tgggtactat tattatccct atcttgatga tagggacaga gtggctaatt
agtatgcctg
   10081 agatcacaca gctactgcag gaggctctca ggatttgaat ccacctggtc
catctggctc
   10141 cagcatctat atgcttttt ttttgttggt ttgtttttga gacggacttt
cgctcttgtt
   10201 gtccaggctg gagtgcaatg gcacaatttc ggctcaccac aacctccacc
tcccaggttc
   10261 aagtgattct cctgcctcag cctcccgagt agctgggatt acaggcatgc
gccaccaggc
   10321 ctggctaatt ttgtattttt agtagagaca gtgtttctct atgttggtca
ggctggtctc
   10381 gcactcccga cctcaggtga tctgcctgct ttggcctccc aaagtgctgg
gattacaggc
   10441 gtgagccacc atgcccggcc agcatctata atatatgcta aaccttaccc
acagctgcct
   10501 ctgtcttggg gtcagggttc ttgaatggtc tgggccagcc tgagttagga
gtgggaagag
   10561 gaagaggagg cacgcgccaa agtgttcttc ccgcctgacc gagtcctctg
cgcctatgag
   10621 gaaggtgggc accgctgtca ccctgtttcc caggaagcca gcaggccag
ggagatactg
   10681 ggatttgcca aaggctcaca gcgagcaagc agcagtgggt gctggctcct
caccactcag
   10741 cctggcacac actgtctctg agcagacctg ggagaaggca tgtgaaaccc
acctagccct
   10801 ggctggaaga gaagtggggg agtggaaatg aaaagtgggg actgggagga
gctgcccacg
```

Figure 2 (cont)

```
10861 tgccctccat ggttccagga tggcactttc atgctgggag tgagcttgcc
ctgtgccagg
10921 ctgtcattga gacgttttcc attcaacaac tgtttctcag acaaggcaca
ggcaggttag
10981 ctctcccagg ccactcaagt agtaaggaaa cagatttaaa cccagacaat
ttggctccac
11041 ggctaaggcc cagagagggg tggtgacaag cctagggtca cacagccaca
gccccagagc
11101 taggaactgc tggctagggc aagcagacag ctgaatccta gccaactgga
ggtggagcag
11161 aggtggagcc agggagaccc aggtggcctc
```

METHODS AND COMPOSITIONS FOR PREDICTING DRUG RESPONSES

CROSS-REFERENCE TO RELATED APPLICATIONS

This application is a divisional of U.S. patent application Ser. No. 10/967,879, filed Oct. 18, 2004, now U.S. Pat. No. 7,445,896, which is hereby incorporated by reference in its entirety.

This application was supported in part by NHLBI—Program for Genomic Applications (PGA) grant (U01 HL66682), Program for Genomic Applications (PGA) grant U01 HL66682, NIH General Medical Sciences grant GM068797 and UW NIEHS sponsored Center for Ecogenetics and Environmental Health, grant NIEHS P30ES07033. The government has certain rights in the invention.

FIELD OF THE INVENTION

The present invention relates to methods and compositions for predicting drug responses. In particular, the present invention provides methods and compositions for determining individualized Warfarin dosages based on the presence or absence of polymorphisms in the VKORC1 gene.

BACKGROUND OF THE INVENTION

More than 3 billion prescriptions are written each year in the U.S. alone, effectively preventing or treating illness in hundreds of millions of people. But prescription medications also can cause powerful toxic effects in a patient. These effects are called adverse drug reactions (ADR). Adverse drug reactions can cause serious injury and or even death. Differences in the ways in which individuals utilize and eliminate drugs from their bodies are one of the most important causes of ADRs. Differences in metabolism also cause doses of drugs to be less effective than desired in some individuals.

More than 106,000 Americans die—three times as many as are killed in automobile accidents—and an additional 2.1 million are seriously injured every year due to adverse drug reactions. ADRs are the fourth leading cause of death for Americans. Only heart disease, cancer and stroke cause more deaths each year. Seven percent of all hospital patients are affected by serious or fatal ADRs. More than two-thirds of all ADRs occur outside hospitals. Adverse drug reactions are a severe, common and growing cause of death, disability and resource consumption.

It is estimated that drug-related anomalies account for nearly 10 percent of all hospital admissions. Drug-related morbidity and mortality in the U.S. is estimated to cost from $76.6 to $136 billion annually.

Most prescription drugs are currently prescribed at standard doses in a "one size fits all" method. This "one size fits all" method, however, does not consider important genetic differences that give different individuals dramatically different abilities to metabolize and derive benefit from a particular drug. Genetic differences may be influenced by race or ethnicity, but may also be largely unpredictable without identifying correlating genomics. What is needed are improved methods for predicting an individual's response to a given drug or a particular dosage of a drug.

SUMMARY OF THE INVENTION

The present invention relates to methods and compositions for predicting drug responses. In particular, the present invention provides methods and compositions for determining individualized Warfarin dosages based on the presence or absence of polymorphisms in the VKORC1 gene. Accordingly, in some embodiments, the present invention provides a method, comprising the steps of: providing a sample from a subject; and determining the subject's VKORC1 haplotype, SNP genotype, or SNP in linkage disequilibrium with any diagnostic SNP. In some embodiments, the method further comprises the step of determining the subject's optimal Warfarin dose based on the subject's VKORC1 haplotype (e.g., H1, H2, H7, H8, or H9 haplotypes). In some embodiments, the method further comprises the step of determining the subject's CYP2C9 genotype. In some embodiments, determining the subject's VKORC1 genotype comprises the use of a nucleic acid based detection assay (e.g., a sequencing assay or a hybridization assay). In some embodiments, the method further comprises the step of determining the subject's Clade type (e.g., AA, AB, or BB Clade types).

In other embodiments, the present invention provides a method, comprising the steps of providing a sample from a subject; detecting the genotype of a single nucleotide polymorphism at one or more positions of SEQ ID NO:1 (e.g., positions 381, 3673, 5808, 6484, 6853, 7566, and 9041 or any polymorphism in linkage disequilibrium with these sites); and determining the subject's optimal Warfarin dosage based on said genotype of the single nucleotide polymorphism. In some embodiments, determining the subject's VKORC1 genotype comprises the use of a nucleic acid based detection assay (e.g., a sequencing assay or a hybridization assay).

The present invention further provides a kit for determining a subject's optimal dose of a blood clotting drug (e.g., Warfarin), comprising: a detection assay, wherein the detection assay is capable of specifically detecting the subject's VKORC1 haplotype (e.g., H1, H2, H7, H8, or H9 haplotypes); and instructions for determining the subject's optimal Warfarin dosage. In some embodiments, the kit further comprises reagents for determining the subject's CYP2C9 genotype. In some embodiments, the detection assay is a nucleic acid based detection assay (e.g., a sequencing assay or a hybridization assay). In some embodiments, the kit further comprises instructions for determining the subject's Clade type (e.g., AA, AB, or BB Clade types).

DESCRIPTION OF THE FIGURES

FIG. 2 shows the nucleic acid sequence of the extended genomic reference sequence for the VKORC1 (SEQ ID NO:1) gene.

DEFINITIONS

Figure 1:
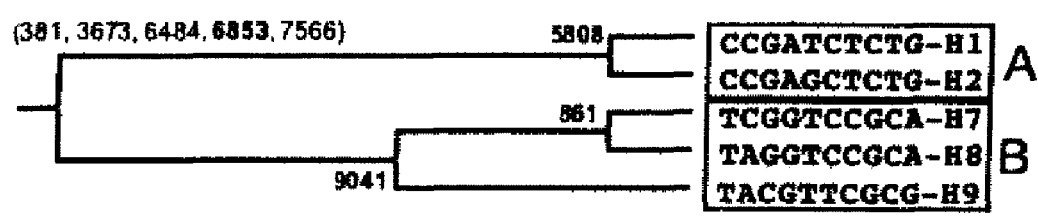
FIG. 1 shows the effect of VKORC1 genealogic clades on clinical warfarin dose. The upper panel shows common haplotypes determined from VKORC1 (H1 (SEQ ID NO:14), H2 (SEQ ID NO:15), H7 (SEQ ID NO:16), H8 (SEQ ID NO:17), and H9 (SEQ ID NO:18)). The lower panel shows Warfarin dosages for clinical patients (n=185) classified according to known functional mutations at the CYP2C9 locus and VKORC1 Clade (A/A (white bars), A/B (grey bars), and B/B (black bars).
Figure 1:
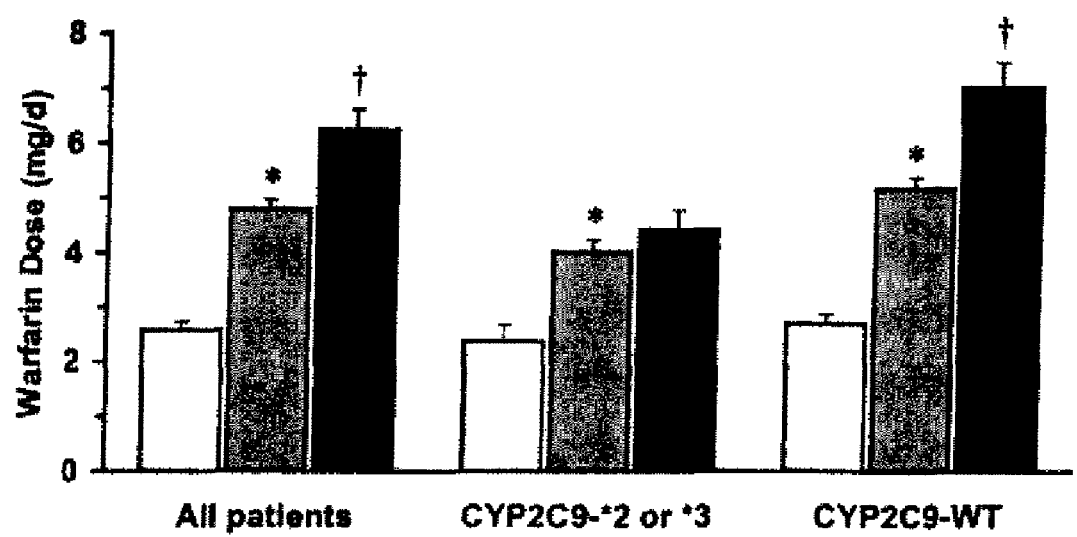

To facilitate an understanding of the present invention, a number of terms and phrases are defined below:

As used herein, the term "single nucleotide polymorphism" or "SNP", refers to any position along a nucleotide sequence that has one or more variant nucleotides. Single nucleotide polymorphisms (SNPs) are the most common form of DNA sequence variation found in the human genome and are generally defined as a difference from the baseline reference DNA sequence which has been produced as part of the Human Genome Project or as a difference found between a subset of individuals drawn from the population at large. SNPs occur at an average rate of approximately 1 SNP/1000 base pairs when comparing any two randomly chosen human chromosomes. Extremely rare SNPs can be identified which may be restricted to a specific individual or family, or conversely can be found to be extremely common in the general population (present in many unrelated individuals). SNPs can arise due to errors in DNA replication (i.e., spontaneously) or due to mutagenic agents (i.e., from a specific DNA damaging material) and can be transmitted during reproduction of the organism to subsequent generations of individuals.

As used herein, the term "linkage disequilibrium" refers to single nucleotide polymorphisms where the genotypes are correlated between these polymorphisms. Several statistical measures can be used to quantify this relationship (i.e. D', $r^2$, etc) reference (See e.g., Devlin and Risch 1995 Sep. 20; 29(2):311-22). In some embodiments, a SNP-SNP pair is considered to be in linkage disequilibrium if $r^2 > 0.5$, As used herein, the term "haplotype" refers to a group of closely linked alleles that are inherited together.

As used herein, the term "haplotype clade" or "clade" refers to any group of haplotypes that are all more similar to one another than any of them is to any other haplotype. Clades may be identified, for example, by performing statistical cluster analysis.

As used herein, the term "subject" refers to any animal (e.g., a mammal), including, but not limited to, humans, non-human primates, rodents, and the like. Typically, the terms "subject" and "patient" are used interchangeably herein in reference to a human subject.

As used herein, the term "non-human transgenic animal" refers to a non-human animal (preferable a mammal, more preferably a mouse) whose endogenous VKORC1 gene has been inactivated (e.g., as the result of a "VKORC1" or a "VKORC1 knock-in") or altered (e.g., contains a polymorphic form of the VKORC1 gene).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 5 kb or more on either end such that the gene corresponds to the length of the full-length mRNA. Sequences located 5' of the coding region and present on the mRNA are referred to as 5' untranslated sequences. Sequences located 3' or downstream of the coding region and present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decreases production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "detection assay" refers to an assay for detecting the presence of absence of variant nucleic acid sequences (e.g., polymorphism or mutations) in a given allele of a particular gene (e.g., the VKORC1 gene).

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

DETAILED DESCRIPTION OF THE INVENTION

Coumarin anticoagulant drugs are the definitive treatment world-wide for the long-term prevention of thromboembolic events. In 2003, a total of 21.2 million prescriptions were written for the oral anticoagulant warfarin in the United States alone. Unfortunately, warfarin poses considerable dose management problems due to a multitude of factors that can modify the anticoagulant effect of the drug: its narrow therapeutic range, discrete ethnic differences in dose requirements and wide inter-individual variability in dosing. These challenges may contribute to the general under-utilization of anticoagulant therapy, particularly in stroke prevention (Fang et al., Arch Intern Med 164, 55-60 (2004); Gage et al., Stroke 31, 822-7 (2000)). Structural gene mutations in cytochrome P450 (CYP) 2C9, the major catabolic enzyme for the more active (S)-enantiomer of warfarin, are a risk factor for adverse outcomes during therapy (Higashi et al., Jama 287, 1690-8 (2002)), and extremely rare mutations in VKORC1 underlie overt warfarin resistance (Rost et al., Nature 427, 537-41 (2004)). The association of a single VKORC1 polymorphism with Warfarin dosage has been described (D'Andrea, Blood, Sep. 9, 2004). However, prior to the present invention, much of the variance in warfarin dose requirement remained unexplained (Gage et al., Thromb Haemost 91, 87-94 (2004)).

Warfarin exerts its antithrombotic effects by inhibiting regeneration of an essential component of clotting factor synthesis—vitamin KH2 (reduced vitamin K)—from vitamin K epoxide (Suttie, Adv Exp Med Biol 214, 3-16 (1987)). This enzyme activity is determined by the recently discovered vitamin K epoxide reductase gene, VKORC1 (Li et al., Nature 427, 541-4 (2004); Rost et al., supra).

Experiments conducted during the course of development of the present invention demonstrated a correlation between certain VKORC1 haplotypes and optimal warfarin dosage. Accordingly, in some embodiments, the present invention provides methods and compositions for determining a subject's optimal Warfarin dose, as well as for related drugs (e.g., drugs that involve the same biological pathway).

I. Personalized Warfarin Dosing

In some embodiments, the present invention provides methods of personalized Warfarin dosing comprising identifying a subject's VKORC1 haplotype or Clade type. As described below (See Experimental Section), experiments conducted during the course of development of the present invention identified a series of VKORC1 polymorphisms associated with optimal Warfarin dosages. Polymorphisms at seven sites (381, 3673, 5808, 6484, 6853, 7566, and 9041) of VKORC1 were identified. The polymorphisms were found to be associated with two low-dose (2.9 and 3.0 mg/d) haplotypes (H1 and H2) and two high-dose (6.0 and 5.5 mg/d) haplotypes (H7 and H9). Thus, the present invention provides compositions, methods, and kits for detecting such polymorphisms and haplotypes, directly or indirectly, by any method, for predicting response to Warfarin and related drugs, selecting drugs dosage, and conducting studies on drug metabolism. These polymorphisms may be detected along with other polymorphisms (e.g., CYP2C9) to enhance the information available to researchers and medical practitioners.

In some embodiments, the methods of the present invention comprise identifying a subject's haplotype and determining the subject's optimal dosage range. The methods of the present invention allow for safer and thus more widespread use of Warfarin and related drugs. Exemplary methods for determining VKORC1 polymorphisms are described below.

1. Direct Sequencing Assays

In some embodiments of the present invention, VKORC1 polymorphic sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, and automated sequencing. The results of the sequencing are displayed using any suitable method. The sequence is examined and the presence or absence of a given SNP or mutation is determined.

2. PCR Assay

In some embodiments of the present invention, variant sequences are detected using a PCR-based assay. In some embodiments, the PCR assay comprises the use of oligonucleotide primers that hybridize only to the variant or wild type allele (e.g., to the region of polymorphism or mutation). Both sets of primers are used to amplify a sample of DNA. If only the mutant primers result in a PCR product, then the patient has the mutant allele. If only the wild-type primers result in a PCR product, then the patient has the wild type allele.

3. Hybridization Assays

In preferred embodiments of the present invention, variant sequences are detected using a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY [1991]). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of DNA polymerases such as AMPLITAQ DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin). Numerous other assays are known in the art.

4. Other Detection Assays

Additional detection assays that are suitable for use in the present invention include, but are not limited to, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884 and 6,183,960, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); INVADER assay, Third Wave Technologies; See e.g., U.S. Pat. Nos. 5,846,717, 6,090,543; 6,001,567; 5,985,557; and 5,994,069; each of which is herein incorporated by reference; cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Bamay Proc. Natl. Acad. Sci. USA 88, 189-93 (1991)); and sandwich hybridization methods (e.g., U.S. Pat. No. 5,288,609, herein incorporated by reference in its entirety).

5. Mass Spectroscopy Assay

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

II. Kits

In some embodiments, the present invention provides kits for the detection of VKORC1 polymorphisms. In some embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results. In some embodiments, individual probes and reagents for detection of VKORC1 polymorphisms are provided as analyte specific reagents. In other embodiments, the kits are provided as in vitro diagnostics.

III. Drug Screening

In some embodiments, the present invention provides drug screening assays (e.g., to screen for anticoagulant drugs). In some embodiments, the screening methods of the present invention utilize polymorphic forms of VKORC1. For example, in some embodiments, the present invention provides methods of screening for compounds that alter (e.g., decrease) the activity of one or more polymorphic forms of VKORC1. In other embodiments, the drug screening methods described below are used to screen compounds known to alter blood clotting with different polymorphic forms of VKORC1.

In one screening method, candidate compounds are evaluated for their ability to alter (e.g., increase or decrease) VKORC1 expression by contacting a compound with a cell expressing VKORC1 and then assaying for the effect of the candidate compounds on expression. In some embodiments, the effect of candidate compounds on expression of VKORC1 is assayed for by detecting the level of VKORC1 mRNA expressed by the cell. mRNA expression can be detected by any suitable method, including but not limited to, those disclosed herein.

In other embodiments, the effect of candidate compounds is assayed by measuring the level of VKORC1 polypeptide. The level of polypeptide expressed can be measured using any suitable method, including but not limited to, those disclosed herein or by monitoring a phenotype (e.g., clotting speed).

In some embodiments, in vitro drug screens are performed using purified wild type or dominant active VKORC1 and binding partners or signaling partners thereof. Compounds are screened for their ability to interact with VKORC1 proteins and inhibit or enhance VKORC1 function or the interaction of VKORC1 with binding partners (e.g., cadherin).

In still further embodiments, cells or transgenic animals having altered (e.g., polymorphic) VKORC1 genes are utilized in drug screening applications. For example, in some embodiments, compounds are screened for their ability to alter blood clotting in VKORC1 mice with a particular polymorphic form of VKORC1.

In yet other embodiments, subjects (e.g., human subject) are enrolled in clinical trials to test dosages of Warfarin or other related drugs (e.g., new drugs). In preferred embodiments, subjects having polymorphic VKORC1 are included in clinical trials to test clotting drugs.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nacl. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al, Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al, Proc. Nacl. Acad. Sci. USA 89:18651869 [1992]) or on phage (Scott and Smith, Science 249:386-390 [1990]; Devlin Science 249:404-406 [1990]; Cwirla et al, Proc. Natl. Acad. Sci. 87:6378-6382 [1990]; Felici, J. Mol. Biol. 222:301 [1991]).

IV. Transgenic Animals Expressing VKORC1 Polymorphic Sequences

The present invention contemplates the generation of transgenic animals comprising an exogenous VKORC1 gene or mutants and variants thereof (e.g., single nucleotide polymorphisms). In preferred embodiments, the transgenic animal displays an altered phenotype (e.g., response to Warfarin or other anticoagulant drugs) as compared to wild-type animals. Methods for analyzing the presence or absence of such phenotypes include but are not limited to, those disclosed herein.

The transgenic animals or natural variants having equivalent genotypes of the present invention find use in drug (e.g., anticoagulant) screens. In some embodiments, test compounds (e.g., a drug that is suspected of being useful as an anticoagulant therapy) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al, Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al, in Manipulating the Mouse Embryo, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Stewart, et al, EMBO J., 6:383 [1987]). Alternatively, infection can be performed at a later stage. Virus or virus-producing cells can be injected into the blastocoele (Jahner et al, Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al, Nature 292:154 [1981]; Bradley et al, Nature 309:255 [1984]; Gossler et al, Proc. Acad. Sci. USA 83:9065 [1986]; and Robertson et al, Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized knock-out gene function or create deletion mutants (e.g., truncation mutants). Methods for homologous recombination are described in U.S. Pat. No. 5,614,396, incorporated herein by reference.

EXPERIMENTAL

The following example is provided in order to demonstrate and further illustrate certain preferred embodiments and aspects of the present invention and are not to be construed as limiting the scope thereof.

Example 1

VKORC1 Polymorphisms

This Example describes the association between VKORC1 polymorphisms and optimal Warfarin dosages.

A. Methods

Clinical and Control Subjects

The initial European American clinical patients used in this study have been previously described (Higashi et al., Jama 287, 1690-8 (2002)) as have most of the European American patients in the replication study (Gage et al., Thromb Haemost 91, 87-94 (2004)). All control DNA population samples were purchased from the human variation collections and the CEPH pedigree samples at the Coriell Cell Repository. The Asian American samples consisted of 96 individuals from the HD100CHI panel (Han People of Los Angeles), 10 Southeast Asians (HD13), 7 Chinese (HD32), and 7 Japanese (from the HD07 panel). The 96 European American samples were selected from the HD100CAU panel with the remaining 23 individuals selected from the parental generation of the CEPH families (for more information on these samples see Table 4). The 96 African American samples were selected from the HD100AA panel.

Sequence Analysis and Genotyping

All clinical samples from the primary European American cohort were resequenced for SNP discovery using PCR amplification of 1 kb fragments covering the entire genomic region of VKORC1 and direct sequencing of the PCR amplicons using standard ABI Big-Dye Terminator sequencing chemistry and run on an ABI 3730XL DNA analyzer. SNPs were identified using the program Polyphred (v. 4.2), along with quality control and review of all SNPs and genotypes by a human analyst. The ten SNPs identified were at position 381(C/T), 861(A/C), 2653(G/C), 3673(A/G), 5808(T/G), 6009(C/T), 6484(C/T), 6853(C/G), 7566(C/T), and 9041(A/G) in the VKORC1 reference sequence (GenBank Accession AY587020; SEQ ID NO:1). A single heterozygous non-synonymous SNP was identified (genomic position 5432 (G/T)-Ala41 Ser) in a European American clinical patient. This patient had the highest overall warfarin maintenance dose (15.5 mg/d) and was excluded from all analyses. No other previously reported nonsynonymous SNPs were identified (Rost et al., Nature 427, 537-41 (2004)). All other control population samples were resequenced using the same methods, but genotyped using only the amplicons containing the 10 common SNPs identified in the European American clinical population.

For the replication study in the secondary European American cohort, four informative SNPs (861, 5808, 6853, and 9041) were used to differentiate between haplotype H1, H2, H7, H8 and H9, based on the genealogical tree in FIG. 1. For each SNP site, PCR primers were designed using Primer Express version 1.5 (ABI, Foster City, Calif.). Pyrosequencing primers were designed using the Pyrosequencing SNP Primer Design Version 1.01 software. Unique localization of the PCR primers was verified using NCBI Blast (available at the Internet site of NCBI). PCR was carried out using Amplitaq Gold PCR master mix (ABI, Foster City, Calif.), 5 pmole of each primer (IDT, Coralville, Iowa), and 1 ng DNA. Pyrosequencing was carried out as previously described (Rose et al., Methods Mol Med 85, 225-37 (2003) using the following primers (5'-3') for each SNP: 861 (A/C), forward=TCTTGGAGTGAGGAAGGCAAT (SEQ ID NO:2), reverse=Biotin—GACAGGTCTGGACAACGTGG (SEQ ID NO:3), internal=CTCAGGTGATCCA (SEQ ID NO:4); 5808 (G/T), forward=Biotin—GGATGCCAGAT-GATTATTCTGGAGT (SEQ ID NO:5), reverse=TCATTATGCTAACGCCTGGCC (SEQ ID NO:6), internal=CAACACCCCCTTC (SEQ ID NO:7); 6853 (G/C), forward=CTTGGTGATCCACACAGCTGA (SEQ ID NO:8), reverse=Biotin—AAAAGACTCCTGTTAGT-TACCTCCCC (SEQ ID NO:9), internal=AGCTAGCTGCTCATCAC (SEQ ID NO:10); 9041 (A/G), forward=TACCCCCTCCTCCTGCCATA (SEQ ID NO:11), reverse=Biotin—CCAGCAGGCCCTCCACTC (SEQ ID NO:12), internal=TCCTCCTGCCATACC (SEQ ID NO:13). Samples of each genotype were randomly selected and repeated to confirm the genotype assignment.

Statistical Methods

Genealogic trees were constructed using the program MEGA and based on the number of differences between haplotypes and the UPGMA clustering method. Haplotypes for each individual sample were estimated using the program PHASE, version 2.0 (Stephens and Donnelly, Am J Hum Genet 73, 1162-9 (2003)), and independent runs were performed for each population studied.

Using the most likely pair of haplotypes estimated for each patient, the association between number of copies of each VKORC1 haplotype (coded 0, 1, 2) and maintenance warfarin dose was assessed on an additive scale. Multiple linear regression was performed using log-transformed maintenance dose, adjusting for the covariates age, sex, race, amiodarone, losartan, and CYP2C9 genotype. Adjusted warfarin doses (and 95% confidence intervals) associated with each additional haplotype copy were estimated by exponentiation of the mean fitted values and standard errors of the linear prediction. In separate analyses, using a generalized linear model score test method (Lake et al., Hum Hered 55, 56-65 (2003)) that additionally takes into account the uncertainty of haplotypes assignments, similar estimates were obtained for mean warfarin dose, and the confidence values were slightly wider.

The Kiruskal-Wallis test, a distribution-free ANOVA, was used to assess differences in maintenance dose among the A/A, A/B and B/B groups. This was done separately for three subsets of the data: (1) for subjects with the *2 or *3 variant, (2) wild type and (3)*2 or *3 and wild type combined. Subjects with a non-A or B haplotype were not used in the analysis. Following the overall chi-square test for differences among the three groups, pairwise comparisons of groups were carried out using the asymptotic normality of the total ranks within each group. The Bonferroni correction for each of the three individual comparisons (A/A vs A/B, A/B vs B/B, and A/A vs B/B) was made to control the overall type I error rate.

Differences between population specific haplotype distributions were done using a $\chi^2$ test.

B. Results

In order to investigate the link between common, non-coding single nucleotide polymorphisms (SNPs) in VKORC1 and warfarin dosing, complete gene resequencing of the VKORC1 gene locus (11.2 kilobases) in a cohort of 185 European American patients receiving long-term warfarin therapy was carried out. All patients had been previously genotyped for known functional CYP2C9 mutations (*2 and *3) that are associated with lower warfarin dose requirements (Higashi et al., Jama 287, 1690-8 (2002); Aithal et al., Lancet 353, 717-9 (1999)). In VKORC1, all clinical samples were resequenced over 5 kilobases in the upstream promoter region, 4.2 kilobases of intragenic (intron and exon) sequence, and 2 kilobases of the 3' downstream region. Ten non-coding SNPs with a minor allele frequency greater than 5% were identified in the European American clinical patients. These SNPs were used to estimate VKORC1 haplotypes that were assigned to each patient. From these 185 patients, five common haplotypes (>5%) were identified—H1, H2, H7, H8, H9 (Table 1).

When each SNP was tested individually, seven sites (381, 3673, 5808, 6484, 6853, 7566, and 9041) were highly significant (p<0.001) and three sites were marginally significant (861, 2653, and 6009, p=0.01, 0.02, and 0.02, respectively) when regressed against daily warfarin maintenance dose. Of the seven highly significant sites, five (381, 3673, 6484, 6853, 7566) are in strong linkage disequilibrium ($r^2$=0.9) and two independent sites (5808 and 9041) are not correlated with any other SNP in this region. Analysis of SNP-SNP interactions also showed significant effects between multiple site combinations, therefore, the association of individual haplotypes with warfarin doses was also quantified. A multiple linear regression analysis using inferred haplotypes for each patient was used to determine the association of haplotype on warfarin dose, while adjusting for genetic and other clinically important covariates (e.g. age, CYP2C9-*2 or *3, etc; see Table 1 and Table 4). Four of the five common haplotypes (frequency>5%) were found to be significantly associated with warfarin dose (p<=0.05) (Table 1). From this analysis, two low-dose (2.9 and 3.0 mg/d) haplotypes (H1 and H2) and two high-dose (6.0 and 5.5 mg/d) haplotypes (H7 and H9) were identified.

A genealogical tree was constructed from the five common haplotypes to identify potential hierarchical haplotype groupings (FIG. 1—upper panel). Two distinct haplotype clades, which were completely segregating at five of the ten VKORC1 SNPs, were identified and designated clade A (H1 and H2) and clade B (H7, H8, and H9). Using this designation, all patients were grouped based on their CYP2C9 genotype and assigned a VKORC1 clade diplotype (i.e. combination of two clades) of A/A, A/B, or B/B. FIG. 1—lower panel). The overall mean (5.1±0.2 mg/d) and range of warfarin maintenance doses were typical of other studies of clinical patients (Aithal et al., supra). Warfarin maintenance dose differed significantly between all three clade diplotype groupings (A/A, A/B, B/B, p<0.001) in the combined patient set (i.e. FIG. 1—All patients), and for the CYP2C9 wild-type (WT) patients—there was an additive effect over the entire warfarin dose range. Overall, the proportion of warfarin dose variance explained by VKORC1 clades A and B was 25%, and was similar to values obtained when considering all VKORC1 SNP sites with interactions. Patients who were carriers of CYP2C9 *2 or*3 mutations showed a similar effect of VKORC1 clade diplotype on warfarin dose (p<0.001 between diplotype A/A and A/B). There was an overall trend towards lower warfarin dose associated with CYP2C9 variant genotype (FIG. 1, lower panel), consistent with the known blunted metabolism of warfarin in carriers of these allelic variants (Rettie et al., Epilepsy Res 35, 253-5 (1999)). The segregation of VKORC1 haplotypes into low and high dose associated clades, independently of CYP2C9*2 and *3, suggests that VKORC1 SNP genotyping have strong predictive power for determining the warfarin dose needed to achieve and maintain therapeutic anticoagulation in the clinical setting.

In order to validate these initial results, a replication study was performed in a larger, independent cohort of warfarin-treated European American patients (n=368). These patients were genotyped using four informative SNPs (861, 5808, 6853, 9041—FIG. 1—upper panel—bold numbers) that resolve all five common haplotypes (H1, H2, H7, H8, and H9) present in the initial European American clinical cohort. Haplotypes were inferred, clade diplotypes assigned, and patients segregated based on their known CYP2C9 genotype. Overall, the results from this larger clinical population recapitulated the salient findings in the index population for all three patient subgroups. In this second cohort, the CYP2C9-WT patients (n=233) and all patients (n=357) showed a significant additive effect across the A/A (3.4±0.26 and 3.2±0.21 mg/d), A/B (4.9±0.17 and 4.4±0.13 mg/d) and B/B (6.7±0.29 and 6.1±0.23 mg/d) clade diplotypes (p<0.05 between A/A and A/B, A/B and B/B).

One variable used in estimating clinical warfarin dose is racial background of the patient (Blann et al., Br J Haematol 107, 207-9 (1999); Gan et al., Int J Hematol 78, 84-6 (2003)). Individuals of Asian-, European-, and African ancestry tend to require, on average, lower (~3.0 mg/d), intermediate (~5.0 mg/d) and higher (~6.5 mg/d) dose, respectively (Yu et al., Qjm 89, 127-35 (1996); Chenhsu et al., Ann Pharmacother 34, 1395-401 (2000); Absher et al., Ann Pharmacother 36, 1512-7 (2002); Gage et al., Thromb Haemost 91, 87-94 (2004)). In order to investigate whether this variation in dose requirement may be due to population specific differences in the distribution of VKORC1 haplotypes, 335 unrelated control individuals, selected from these population ancestries (European, n=119, African, n=96, Asian, n=120) were resequenced and the genotype was determined at each of the 10 SNPs present in the European-descent clinical patients. Haplotype pairs for each individual were inferred, and the population haplotype frequencies determined along with the distribution of clade A and B haplotypes (Table 2). The distribution of common haplotypes (H1, H2, H7, H8, and H9) between the European American clinical and control populations was significantly different (p<0.001), primarily due to an increase in the high dose associated H7 haplotype in clinical patients. This may be due to selection bias in the clinical population resulting from preferential referral, to an academic medical center, from which the patients were recruited.

The five predictive haplotypes accounted for 99% and 96%, of the total haplotypes in the European American clinical and control populations; no significant difference was present based on the distribution of clades A (35% vs 37%) and B (64% vs 58%). The five common haplotypes within the European American population accounted for only 61% of total African American haplotypes. This more diverse distribution of haplotypes in the African American population is consistent with the higher genomic sequence diversity found in African-descent populations (Przeworski et al., Trends Genet 16, 296-302 (2000); Crawford et al., Am J Hum Genet 74, 610-22 (2004)). These population-specific haplotype differences may be due to demographic effects such geographic selective pressures, migration, or bottlenecks, and have been observed for other medically relevant genes (e.g. ADRB2, (Drysdale et al., Proc Natl Acad Sci USA 97, 10483-8 (2000)). The African and Asian American populations showed significant differences in clade A and B frequencies (p<0.001) compared to the European American control population. The frequency of clade A haplotypes was higher among the Asian American population (89%) and lower in the African American population (14%) compared to the European American control population (37%). Because clade A haplotypes predict the low warfarin dose phenotype (Table 1), ethnic differences in VKORC1 haplotype frequency parallel the clinical experience of population differences in warfarin maintenance dose requirements. Thus, this example describes population specific differences in haplotype distribution that are a major contributor to the variation in warfarin maintenance dose requirements between racial groups.

The molecular mechanism(s) by which these haplotypes, or the individual SNP alleles that comprise them, determine warfarin dose remain undefined. Two of these SNPs (381 and 3673) are present in the 5' upstream promoter region, two in the first intron (5808 and 6484) and one (9041) in the 3' untranslated region (UTR). None of the significantly associated SNPs are present in highly conserved non-coding sequence present in mouse or rat. The present invention is not limited to a particular mechanism. Indeed, an understanding of the mechanism is not necessary to practice the present invention. Nonetheless, it is contemplated that SNPs in the 3' UTR may affect mRNA folding and stability (Durrin, L. K., Haile, R. W., Ingles, S. A. & Coetzee, G. A. Vitamin D receptor 3'-untranslated region polymorphisms: lack of effect on mRNA stability. Biochim Biophys Acta 1453, 311-20 (1999); Carter, A. M., Sachchithananthan, M., Stasinopoulos, S., Maurer, F. & Medcalf, R. L. Prothrombin G20210A is a bifunctional gene polymorphism. Thromb Haemost 87, 846-53 (2002)), which could alter VKORC1 expression and possibly warfarin response. The present invention is not limited to a particular mechanism. Indeed, an understanding of the mechanism is not necessary to practice the present invention.

Nonetheless, it is contemplated that the strong association of individual haplotypes with warfarin dose also suggests that a functional interaction between SNP alleles carried on the same haplotype may be contributing to the observed results.

In summary, this Example describes VKORC1 noncoding SNPs and haplotypes that are strongly associated with warfarin dose. These haplotypes group into higher order clades that segregate patients into low, intermediate and high warfarin maintenance doses. The VKORC1 gene-warfarin dose association is independent of CYP2C9 genotype, and explains 23%-25% of the variability in the warfarin dose. Genotyping for these VKORC1 SNPs and haplotypes provides more accurate initial dosing and reduces the amount of time to stable anticoagulation, thereby improving the safety, effectiveness, and hospitalization costs associated with warfarin therapy.

TABLE 1

Average warfarin maintenance dose requirement based on VKORC1 haplotype.

| Haplotype | Haplotype Sequence | Frequency | Average maintenance dose for homozygous patients (mg/d)* |
|---|---|---|---|
| H1 | CCGATCTCTG (SEQ ID NO: 14) | 0.12 | 2.9 (2.2-3.7) |
| H2 | CCGAGCTCTG (SEQ ID NO: 15) | 0.24 | 3.0 (2.5-3.6) |
| H7 | TCGGTCCGCA (SEQ ID NO: 16) | 0.35 | 6.0 (5.2-6.9) |
| H8 | TAGGTCCGCA (SEQ ID NO: 17) | 0.08 | 4.8 (3.4-6.7) |
| H9 | TACGTTCGCG (SEQ ID NO: 18) | 0.21 | 5.5 (4.5-6.7) |

*Adjusted for race, age, sex, amiodarone, losartan, and CYP2C9 variant genotype. Warfarin dose effect for each haplotype is shown as: Mean (95% confidence interval). p-values for each haplotype were H1, $p < 0.0001$; H2, $p < 0.001$; H7, $p < 0.001$; H8, $p = 0.76$, and H9 $p = 0.05$). n = 185 clinical samples.

Note:
For each haplotype sequence the alleles are listed in sequential order across the VKORC1 gene - 381, 861, 2653, 3673, 5808, 6009, 6484, 6853, 7566, and 9041.

TABLE 2

VKORC1 haplotype distributions in European-, African- and Asian American populations.

| Haplotype | Haplotype Sequence | European Clinic | European Controls | African Controls | Asian Controls |
|---|---|---|---|---|---|
| 1 | CCGATCTCTG (SEQ ID NO: 14) | 43 (0.12) | 28 (0.12) | 14 (0.07) | 213 (0.89) |
| 2 | CCGAGCTCTG (SEQ ID NO: 15) | 88 (0.24) | 61 (0.26) | 12 (0.06) | 0 (0.00) |
| 3 | CCGGTCCCCG (SEQ ID NO: 19) | 2 (0.01) | 3 (0.01) | 27 (0.14) | 0 (0.00) |
| 4 | CCGGTCCGTG (SEQ ID NO: 20) | 1 (0.00) | 0 (0.00) | 11 (0.06) | 0 (0.00) |
| 5 | TCGAGCTCTG (SEQ ID NO: 21) | 1 (0.00) | 5 (0.02) | 0 (0.00) | 0 (0.00) |
| 6 | TCGGTCCGCG (SEQ ID NO: 22) | 0 (0.00) | 0 (0.00) | 15 (0.08) | 0 (0.00) |
| 7 | TCGGTCCGCA (SEQ ID NO: 16) | 132 (0.35) | 49 (0.21) | 80 (0.42) | 25 (0.10) |
| 8 | TAGGTCCGCA (SEQ ID NO: 17) | 28 (0.08) | 34 (0.14) | 2 (0.01) | 0 (0.00) |
| 9 | TACGTTCGCG (SEQ ID NO: 18) | 77 (0.21) | 56 (0.24) | 11 (0.06) | 0 (0.00) |
| OTHER | — | 0 (0.00) | 2 (0.01) | 20 (0.10) | 2 (0.01) |
| | Clade A (1, 2) | 131 (0.35) | 89 (0.37) | 26 (0.14) | 213 (0.89) |
| | Clade B (7, 8, 9) | 237 (0.64) | 139 (0.58) | 93 (0.47) | 25 (0.10) |
| | TOTAL (A & B) | 340 (0.99) | 194 (0.96) | 119 (0.61) | 238 (0.99) |
| | Total Chromosomes (2N) | 372 | 238 | 192 | 240 |
| | Total Individuals (N) | 186 | 119 | 96 | 120 |

Note:
Haplotype alleles at each position are listed in the same order as Table 1. For each population the number of inferred haplotypes is listed. Numbers in parentheses denote proportion of individuals with given haplotype.

TABLE 3

VKORC1 SNP genotype tests and maintenance warfarin dose

| Genotype | # (%) | Mean dose (95% CI) | Unadjusted P-value | Adjusted P-value* |
|---|---|---|---|---|
| VKORC1 381 | | | <0.001 | <0.001 |
| C/C | 49 (42) | 5.4 (4.7-6.3) | | |
| C/T | 56 (47) | 4.6 (4.2-5.1) | | |
| T/T | 13 (11) | 2.3 (1.8-2.9) | | |
| VKORC1 861 | | | 0.01 | 0.01 |
| A/A | 58 (48) | 4.0 (3.5-4.5) | | |
| A/C | 49 (40) | 5.0 (4.4-5.7) | | |
| C/C | 14 (12) | 5.3 (4.2-6.6) | | |
| VKORC1 2653 | | | 0.009 | 0.02 |
| G/G | 115 (64) | 4.3 (3.9-4.7) | | |
| G/C | 59 (33) | 4.9 (4.3-5.6) | | |
| C/C | 7 (4) | 6.6 (4.3-10.2) | | |
| VKORC1 3673 | | | <0.001 | <0.001 |
| A/A | 77 (43) | 5.5 (4.9-6.2) | <0.001 | <0.001 |
| G/A | 81 (45) | 4.6 (4.2-5.0) | 0.004 | 0.005 |
| G/G | 22 (12) | 2.6 (2.2-3.1) | <0.001 | <0.001 |
| VKORC1 5808 | | | <0.001 | 0.0001 |
| T/T | 104 (60) | 5.2 (4.8-5.7) | | |
| T/G | 60 (35) | 4.0 (3.6-4.6) | | |
| G/G | 9 (5) | 2.6 (2.0-3.5) | | |
| VKORC1 6009 | | | 0.007 | 0.02 |
| C/C | 110 (62) | 4.3 (3.9-4.7) | | |
| C/T | 61 (34) | 5.0 (4.4-5.6) | | |
| T/T | 7 (4) | 6.6 (4.3-10.2) | | |
| VKORC1 6484 | | | <0.001 | <0.001 |
| C/C | 77 (42) | 5.5 (4.9-6.2) | | |
| C/T | 83 (46) | 4.5 (4.1-4.9) | | |
| T/T | 22 (12) | 2.6 (2.2-3.1) | | |
| VKORC1 6853 | | | <0.001 | <0.001 |
| C/C | 72 (41) | 5.5 (4.8-6.1) | | |
| C/G | 80 (46) | 4.4 (4.1-4.8) | | |
| G/G | 22 (13) | 2.6 (2.2-3.0) | | |
| VKORC1 7566 | | | <0.001 | <0.001 |
| C/C | 74 (42) | 5.4 (4.8-6.1) | | |
| C/T | 83 (47) | 4.5 (4.1-4.9) | | |
| T/T | 21 (12) | 2.6 (2.2-3.0) | | |
| VKORC1 9041 | | | <0.001 | <0.001 |
| A/A | 56 (32) | 3.7 (3.3-4.3) | | |
| G/A | 87 (50) | 4.8 (4.4-5.3) | | |
| G/G | 30 (17) | 5.9 (5.2-6.6) | | |

*Adjusted for age, race, sex, amiodarone, losartan, CYP*2, and CYP*3.
P-values were derived from likelihood ratio test statistics of linear regression models in which the number of SNP alleles was coded 0, 1, 2 to represent an additive or co-dominant genetic model of inheritance.

TABLE 4

Characteristics of 185 European American Warfarin Clinic Patients

| Characteristic | N (%) or mean ± SD (range) |
|---|---|
| Sex | |
| Male | 121 (65) |
| Female | 64 (35) |
| Race | |
| White | 179 (97) |
| Hispanic | 6 (3) |
| Age, years (range) | 59.9 ± 15.7 (19-88) |
| Cigarette smoke | 25 (14) |
| Diagnosis | |
| Atrial fibrillation | 95 (52) |
| Arrhrhythmia | 81 (44) |
| Congestive heart failure | 77 (42) |
| Venous thromboembolic disease | 40 (22) |
| Dilated cardiomyopathy | 37 (20) |
| Valvular disease | 13 (7) |
| Hypertension | 85 (46) |
| Diabetes type | 41 (22) |
| Malignancy | 27 (15) |
| Medication use | |
| Amiodarone | 24 (13) |
| Losartan | 17 (9) |
| Torsemide | 11 (6) |
| Acetaminophen | 52 (28) |
| Vitamin C | 27 (15) |
| Vitamin E | 25 (14) |
| Maintenance warfarin dose, mg/day | 5.1 ± 2.5 |
| Follow-up, days | |
| Mean | 831 |
| Median | 545 |
| Range | 14-4032 |

TABLE 5

Comparison of daily warfarin dose and clade diplotype between the two European American clinical cohorts.

| | AA | | | AB | | | BB | | |
|---|---|---|---|---|---|---|---|---|---|
| | ALL | *2 or *3 | WT | ALL | *2 or *3 | WT | ALL | *2 or *3 | WT |
| Index Population (n = 185) - Seattle - University of Washington | | | | | | | | | |
| Average | 2.58 | 2.37 | 2.69 | 4.79 | 4.00 | 5.15 | 6.23 | 4.40 | 7.00 |
| StDev | 0.82 | 0.87 | 0.79 | 1.83 | 1.10 | 1.98 | 2.71 | 1.41 | 2.77 |
| SEM | 0.17 | 0.31 | 0.20 | 0.20 | 0.21 | 0.26 | 0.32 | 0.30 | 0.38 |
| n | 23 | 8 | 15 | 86 | 27 | 59 | 74 | 22 | 52 |
| Replication Population (n = 368) - St. Louis - Washington University | | | | | | | | | |
| Average | 3.20 | 2.78 | 3.35 | 4.42 | 3.61 | 4.90 | 6.11 | 5.00 | 6.68 |
| StDev | 1.40 | 1.21 | 1.46 | 1.75 | 1.40 | 1.77 | 2.71 | 2.08 | 2.83 |
| SEM | 0.21 | 0.35 | 0.26 | 0.13 | 0.18 | 0.17 | 0.23 | 0.30 | 0.29 |
| n | 44 | 12 | 32 | 170 | 63 | 107 | 143 | 49 | 94 |

Note:
some individuals were not able to be classified within the A or B clades

What is claimed:

1. A method of predicting a human subject's response to warfarin, said method comprising:
   providing a sample from a human subject;
   determining, in the subject's VKORC1 gene, the presence of an adenosine or guanine at the nucleotide corresponding to position 3673 of SEQ ID NO:1 in the sample from the subject; and
   predicting, based on the subject's genotype of A/A, A/G, or G/G at position 3673, the human subject's response to warfarin.

2. The method according to claim 1, wherein said determining comprises:
   sequencing a nucleic acid molecule from the sample at least the nucleotide corresponding to position 3673 of SEQ ID NO: 1.

3. The method according to claim 1, wherein said determining comprises:
   detecting, in a hybridization assay, an ability of a nucleic acid molecule from the sample to hybridize to an oligonucleotide probe.

4. The method according to claim 1, wherein said determining comprises:
   detecting, in a PCR-based assay, an ability of oligonucleotide primers to amplify a nucleic acid molecule from the sample.

5. The method according to claim 1, wherein the nucleotide corresponding to position 3673 is adenosine.

6. The method according to claim 1, wherein the nucleotide corresponding to position 3673 is guanine.

7. A method of determining a suitable dose of warfarin for a human subject, said method comprising:
   providing a sample from a human subject;
   determining, in the subject's VKORC1 gene, the presence of an adenosine or guanine at the nucleotide corresponding to position 3673 of SEQ ID NO:1 in the sample from the subject; and
   identifying a suitable dose of warfarin for the subject based on the subject's genotype of A/A, A/G, or G/G at position 3673.

8. The method according to claim 7, wherein said determining comprises:
   sequencing a nucleic acid molecule from the sample at least the nucleotide corresponding to position 3673 of SEQ ID NO: 1.

9. The method according to claim 7, wherein said determining comprises:
   detecting, in a hybridization assay, an ability of a nucleic acid molecule from the sample to hybridize to an oligonucleotide probe.

10. The method according to claim 7, wherein said determining comprises:
    detecting, in a PCR-based assay, an ability of oligonucleotide primers to amplify a nucleic acid molecule from the sample.

11. The method according to claim 7, wherein the nucleotide corresponding to position 3673 is adenosine.

12. The method according to claim 7, wherein the nucleotide corresponding to position 3673 is guanine.

13. The method according to claim 7 further comprising:
    administering warfarin to the subject at a dosage determined from said identifying.

14. A method comprising:
    providing a sample from a human subject receiving warfarin therapy;
    determining, in the subject's VKORC1 gene, the presence of an adenosine or guanine at the nucleotide corresponding to position 3673 of SEQ ID NO:1 in the sample from the subject; and
    establishing a correlation between the subject's genotype of A/A, A/G, or G/G at position 3673 with the subject's maintenance warfarin dose.

15. The method according to claim 14, wherein the nucleotide corresponding to position 3673 is adenosine.

16. The method according to claim 14, wherein the nucleotide corresponding to position 3673 is guanine.

17. A method of predicting a dose range of warfarin for a human patient, comprising:
    investigating the nucleotide at the 3673 position of the VKORC1 gene of the patient; wherein the nucleotide is investigated by using an oligonucleotide that specifically hybridizes with the promoter of the VKORC1 gene;
    determining whether the patient requires a higher or lower dose of warfarin based on the nucleotide at the 3673 position, wherein homozygous AA, heterozygous AG, and homozygous GG at this position indicate that the patient requires a lower, intermediate, or higher warfarin dose respectively; and
    predicting a warfarin dosage range based on said determining whether the patient requires a higher or lower dose of warfarin.

* * * * *

SEQUENCE LISTING

<160> NUMBER OF SEQ ID NOS: 22

<210> SEQ ID NO 1
<211> LENGTH: 11190
<212> TYPE: DNA
<213> ORGANISM: Homo sapiens

<400> SEQUENCE: 1

| | | | | | | |
|---|---|---|---|---|---|---|
| cagaggacaa | catagatagg | ttcggagact | actcagagaa | agggagagag | aatgctaggt | 60 |
| tatctttcag | ctgttttagc | tgcttattgt | tccagcttta | gccaccatct | gactgcaatt | 120 |
| gtatgagcca | gaaatagcca | ggtaaaattg | tcttcccaaa | ttcctagtgc | acaaaaactg | 180 |
| tcagaggctg | ggggcagtgg | ctcactcctg | taatcccagc | agcactttgg | gaagccaggg | 240 |
| tgggagaact | gcttgagccc | aggagttaga | ggcaacataa | caacaactca | tctctaatga | 300 |
| aaaaaaaaa | aaaagaaaga | aaaggccag | gcacagtggc | tcacgcctgt | aatcccagca | 360 |
| ctttaggaag | ccaaggaggg | tggatcatga | ggtcaggagt | ttgagaccag | cctggccaat | 420 |
| atggtgaaac | cccgtctcta | ctaaaaacac | aaaaatcagc | cacgcatagt | ggctggtgcc | 480 |
| tgtaatcaca | gctactcagg | aggctaaggc | aggagaatca | cttgaatccg | ggaggcagag | 540 |
| gttgcagtga | gccgagattg | caccactgca | tttcagcctg | ggcagcagag | tgggactgtc | 600 |
| tcacattaat | taattaattg | attaaatgct | agaagaaaat | atggtcaaaa | tcttttataa | 660 |
| ctcttggagt | gaggaaggca | atctcggctc | actacaactt | ccacctcccg | ggttcaaatg | 720 |
| attctcctgc | ctcagcctcc | tgagtagctg | ggattacagg | cacccaccac | catgcccggc | 780 |
| taatttttgt | attttttagta | gagacgaggt | ttcgccatgt | tggccaagct | tgtcttaaac | 840 |
| tcctgacctc | aggtgatcca | cccacctcag | cctcccaaat | tgctgggatt | acaggcatga | 900 |
| gccaccatgc | cccgcctaat | tttaaaaatg | tttataaaga | cagagtctta | ccacgttgtc | 960 |
| cagacctgtc | tcaaactcct | gggctcaagt | cattgtcttg | tctcagcctc | ccaaagttct | 1020 |
| gggactacag | gtgtgcacca | ccacacctgg | ctaattttgt | ttatttttta | tagagtgagg | 1080 |
| gtctccctgt | gttgtccagg | gtgtctcaaa | ctcctgggct | caagtggtcc | tcctgcctca | 1140 |
| gcctcccaaa | gtgctgggat | tataggcata | agccactgca | cctggcccca | gtgtgtgtct | 1200 |
| tctgaggcta | agtcataaag | agattgcggc | ttctattttg | cttcctctta | gatcactcat | 1260 |
| tctgggggaa | accaacaata | aataacagga | acacaccagg | agatcagaga | aagctgagat | 1320 |
| acaggcctaa | tgcccagtcc | tctgtattca | tttctaattg | ctgctgtaac | aagttactgc | 1380 |
| acatttaatg | atgtaaaaca | acacaaattt | atcttacagt | tctgtagctt | agaagtctga | 1440 |
| cagagtctca | ctgggctgaa | atcaagatgt | tgatagttcc | ttcccggtga | ctctagagtg | 1500 |
| agaatccagt | tctttaccct | ttcttgcctt | tagaggccac | ccgtatttat | tagctcacaa | 1560 |
| tccccttcct | ccatcttcaa | accagaaaca | ttgcagctct | ctgtgtcttt | tttcttact | 1620 |
| cacatctccc | tctgactttc | ttctgccatc | ctccttcatt | ttttaaggac | ccctgtgggc | 1680 |
| caggcatggt | ggcttatgcc | tgtaatccca | gcactttgag | aggcggaggc | aggcgggtca | 1740 |
| cctgaggtca | ggagttccag | accagcctgg | ccaacatggc | aaaaccccat | ctccactgaa | 1800 |
| aatacaaaaa | ttgggccagg | cacggcggct | cacacccgta | atcccatac | tttgagaggc | 1860 |
| tgaggcaggt | ggatcacttg | aggtcaggag | ttcaagacca | gcctggccaa | catggtgaaa | 1920 |
| tcccgtctct | actaaaaaaa | aaaaaattta | caataattag | tcaggcgtgg | tggccagcac | 1980 |
| ctataatccc | agctacttgg | gaggttgagg | cacaagaatt | gcttgaaccc | gagaggggga | 2040 |

```
ggttgcagtg agctgagatt gcaccaccgt actccagcct ggatgacaga gcaagactct    2100
gtctcaaaat aaaaattaag ataaataata aaaataaat aaaaatcagc aaattaggcc    2160
aggtgtggtg gtggctcatg cctgtactcc cagcactttg aggtgggaag gttgcttgaa    2220
accagaagtt tagaccagcc tgggaaacaa agtgagaccc catctctaca aaaataaaaa    2280
taaattagcc aggtgtggtg ggacgtactt gtactcctag ctactaggga ggctgaggtg    2340
caagaatcgc ttgaacctgg gagacggagg ttgcagtgag ttatgacagt gccactacac    2400
tccagcctgg gtgtcaaggg tcttttgaaaa aataaacaaa ataggctggg cgtggtggct    2460
tacacttgta atcccagcac tttgggaggc tgaggcaggc agatcacaaa gtcaggagtt    2520
cgagaccagc ctggccaaca cagtgaaacc ccgtctctac taaaaataca aaaattagcc    2580
aggcatggtt gcacgcgcct gtagtcccaa ctgctcggga ggctgaggca ggagaatggc    2640
ttgaacctgg ggggggcgg aagttataat gagccaagat tgtgccactg cactccagcc    2700
taggcaacag agcgagactc cgtctcaaaa ataaaaataa aaataaatca atagagcctg    2760
gtatgatggc tcacgcctat aatcccagca ctttgggagg cccaggtggg tggatcatct    2820
gaggtcagga gtttgagacc agcctgacca acatggagaa accccatctc tactaaaaat    2880
acaaaaaatt agccaggcgt ggtggcacat gcctataatc ccagctactc aggagcctga    2940
ggcaggagaa tcgctttaac cggggaggtg gaggttgcgg tgagtcgaga tagcaccatt    3000
gcattctagc ctgggcaaca agagcaaaac tccatctcaa aaataaataa ataaatagat    3060
agataggctg gcacggtgg ctcacgcctg taatcccagc actttgggag gccgaggtgg    3120
gcggatcacc tgaggtcagg agttcaagac cagcctggcc aatatagcga aaccctgtct    3180
ctactaaaaa tttaaaaat tagccaggca tgatggcggg tgcctgtaat cccagctact    3240
cgggaggctg aggcaggaga atctctcgaa cctggcaggc ggaggttgca gtgagccgag    3300
atcacaccat tgcactccag ttgggcaaca agagcgaaac tccacctcaa aaacaaaata    3360
aaataaaata aaatcaggag attggtcagc ttaattccat ctgcaacctt aattcccttt    3420
tggccattta acctatcata ttcacaagtt ccagggattc atgcagggac atctttggtg    3480
accattattc tgtctaccac actctctaga agagagtaga tgtgagaaac agcatctgga    3540
gagggaggag ccagcaggag agggaaatat cacagacgcc agaggaagag agttcccaga    3600
agggtaggtg caacagtaag ggatccctct gggaagtcaa gcaagagaag acctgaaaaa    3660
caaccattgg ccgggtgcgg tggctcacgc ctataatcct agcattttgg gaggccgagg    3720
tgggtggatc acttgaggtc aggagtttaa gacaagcctg ccaacatgg tgaaaccctg    3780 tctctactaa aaatacaaaa attagccaga catggtggca ggcacctgta gtccaaacta    3840
cttgggaggc tgaggcacga gaaccacttg aaccctggag gcggaagttg cagtgagccg    3900
agatggcacc gctgcactcc agcctgggcg acagagtgag actccgtctc aaaataagta    3960
aataaataaa taaataacca ttgggtctag cgtcttggtg acaccagcca ctaggtgtca    4020
gggcaatgct ggaggcagca gctagtttat ggcgtgggca gcaaggaaga agtgaggaag    4080
tagagactgg gagtgtagaa tctttccaaa aacttgaatg tggagggta gatgggataa    4140 tgccgggaga ggaggctggt gaaggacctc ttagtgaagg gagatttgtt gctgtttctg    4200
agatgggaaa gagaaacaag ttgcagtgta gatgggagg atggagaggt tgaaggtgta    4260
ggagagatgg gtcaccatca gatgggacgt ctgtgaagga gagacctcat ctggcccaca    4320
gcttggaaag gagagactga ctgttgagtt gatgcaagct caggtgttgc caggcgggcg    4380
ccatgatagt agagaggtta ggatactgtc aagggtgtgt gtggccaaag gagtggttct    4440
```

```
gtgaatgtat gggagaaagg gagaccgacc accaggaagc actggtgagg caggacccgg    4500
gaggatggga ggctgcagcc cgaatggtgc ctgaaatagt ttcagggaa atgcttggtt     4560 cccgaatcgg atcgccgtat tcgctggatc ccctgatccg ctggtctcta ggtcccggat    4620
gctgcaattc ttacaacagg acttggcata gggtaagcgc aaatgctgtt aaccacacta   4680 acacacttttt ttttttcttt tttttttttg agacagagtc tcactctgtc ggcctggctg   4740
gagtgcagtg gcacgatctc ggctcactgc aacctccggc tccccggctc aagcaattct   4800
cctgcctcag cctcccgagt agctgggatt acaggcatgt gccaccacgc ccggctaatt   4860
tttgtatttt tagttgagat ggggtttcac catgttggcg aggctggtct tgaactcctg   4920
acctcaggta atccgccagc ctcggcctcc caaagtgctg ggattacaag cgtgagccac   4980
cgtgcccggc caacagtttt taaatctgtg gagacttcat ttcccttgat gccttgcagc   5040
cgcgccgact acaactccca tcatgcctgg cagccgctgg ggccgcgatt ccgcacgtcc   5100 cttaccgct tcactagtcc cggcattctt cgctgttttc ctaactcgcc cgcttgacta    5160
gcgccctgga acagccattt gggtcgtgga gtgcgagcac ggccggccaa tcgccgagtc   5220
agagggccag gaggggcgcg gccattcgcc gcccggcccc tgctccgtgg ctggttttct   5280
ccgcgggcgc ctcgggcgga acctggagat aatgggcagc acctggggga gccctggctg   5340
ggtgcggctc gctctttgcc tgacgggctt agtgctctcg ctctacgcgc tgcacgtgaa   5400
ggcggcgcgc gcccgggacc gggattaccg cgcgctctgc gacgtgggca ccgccatcag   5460
ctgttcgcgc gtcttctcct ccaggtgtgc acgggagtgg gaggcgtggg gcctcggagc   5520
agggcggcca ggatgccaga tgattattct ggagtctggg atcggtgtgc ccggggaacg   5580
gacacggggc tggactgctc gcggggtcgt tgcacagggg ctgagctacc cagcgatact   5640
ggtgttcgaa ataagagtgc gaggcaaggg accagacagt gctggggact gggattattc   5700
cggggactcg cacgtgaatt ggatgccaag gaataacggt gaccaggaaa ggcggggagg   5760
caggatggcg gtagagattg acgatggtct caaggacggc gcgcaggtga aggggggtgt   5820
tggcgatggc tgcgcccagg aacaaggtgg cccggtctgg ctgtgcgtga tggccaggcg   5880
ttagcataat gacggaatac agaggaggcg agtgagtggc cagggagctg agattctgg    5940 ggtccagggc aaagataatc tgcccccgac tcccagtctc tgatgcaaaa ccgagtgaac   6000
cgttatacca gccttgccat tttaagaatt acttaagggc cgggcgcggt ggcccactcc   6060
tgtaatccca gcactttggg aggccgaggc ggatggatca cttgaagtca ggagttgacc   6120
agcctggcca acatggtgaa agcctgtctc taccaaaaat agaaaaatta atcgggcgct   6180
atggcgggtg ccttaatccc agctactcgg gggggctaag gcaggagaat cgcttgaacc   6240
cgggaggcgg aggtttcagt gagccgagat cgcgccactg cactccagcc tgggccagag   6300
tgagactccg tctcaaaaaa aaaaaaaaaa aaaaaaaaa agagacttac ttaaggtcta    6360
agatgaaaag cagggcctac ggagtagcca cgtccgggcc tggtctgggg agaggggagg   6420
atagggtcag tgacatggaa tcctgacgtg gccaaggtg cccggtgcca ggagatcatc    6480
gacccttgga ctaggatggg aggtcgggga acagaggata gcccaggtgg cttcttggaa   6540
atcacctttc tcgggcaggg tccaaggcac tgggttgaca gtcctaacct ggttccaccc   6600 cacccaccc ctctgccagg tggggcaggg gtttcgggct ggtggagcat gtgctgggac    6660
aggacagcat cctcaatcaa tccaacagca tattcggttg catcttctac acactacagc   6720
tattgttagg tgagtggctc cgccccctcc ctgcccgccc cgcccgccc ctcatccccc    6780 ttggtcagct cagcccccact ccatgcaatc ttggtgatcc acacagctga cagccagcta  6840
```

```
gctgctcatc acggagcgtc ctgcgggtgg ggatgtgggg aggtaactaa caggagtctt    6900
ttaattggtt taagtactgt tagaggctga agggccctta agacatcct aggtccccag     6960
gttttttgtt tgttgttgtt ttgagacagg gtctggctct gttgcccaaa gtgaggtcta    7020
ggatgccctt agtgtgcact ggcgtgatct cagttcatgg caacctctgc ctccctgccc    7080
aagggatcct cccaccttag cctcccaagc agctggaatc acaggcgtgc accactatgc    7140
ccagctaatt tttgttttg ttttttttg gtagagatgg tgtctcgcca tgttgcccag      7200
gctggtctca agcaatctgt ctgcctcagc ctcccaaagt gctggggga ttacaggcgt     7260
gagctaccat gccccaccaa cacccccagtt ttgtggaaaa gatgccgaaa ttccttttta   7320
aggagaagct gagcatgagc tatctttgt ctcatttagt gctcagcagg aaaatttgta    7380
tctagtccca taagaacaga gagggaacc aagggagtgg aagacgatgg cgccccaggc    7440
cttgctgatg ccatatgccg gagatgagac tatccattac cacccttccc agcaggctcc    7500
cacgctccct ttgagtcacc cttcccagct ccagagaagg catcactgag ggaggcccag    7560
caccacggtc ctggctgaca catggttcag acttggccga tttatttaag aaatttatt    7620
gctcagaact ttccctccct gggcaatggc aagagcttca gagaccagtc ccttggaggg    7680
gacctgttga agccttcttt tttttttttt ttaagaaata atcttgctct gttgcccagg    7740
ctggagtgca gtggcacaat catagctcac tgtaacctgg ctcaagcgat cctcctgagt    7800
agctaggact ataggcatgt cactgcaccc agctaatttt tttttttttt tttttttttt   7860
ttttgcgaca tagtctcgct ctgtcaccag gctggagtgc agtggcacga tcttggctca    7920
ctgcaacctc tgcctcccgg gttcaagcaa ttttcctgcc tcagcctcct gagtagctgg    7980
gactacaggc gcgtgtcacc acgcccagct aattttgta tttttagtgg agacagggtt     8040
tcaccatgtt ggctaggatg gtctcaatct cttgacctgg tgatccatcc gccttggcct    8100
cccaaagtgc taggattaca ggcgtgagtc aacctcaccg gcattttttt tttgagacg     8160
aagtcttgct cttgctgccc aagctggaat gtggtggcat gatctcggct cactgcaacc    8220
tccacctcct aggttcaagc gattctccac cttagcctcc ccagcagctg ggattacagg    8280
tgcccatcaa cacaccggc taattttgt atttttatta gagatggggt tttgccatgt      8340
tggccaggct gctctcgaac tcctaacctc aggtgatcca cccccattgg cctcccaaaa    8400
tactgggatt acaggcatga gccaccgtgc ccagctgaat ttctaaattt ttgatagaga    8460
tcgggtcttt ctatgttgcc caagctggtc ttgaactcct agcctaaagc agtcttccca    8520
cctcggcctc ccagagtgtt tggaatacgt gcgtaagcca ccacatctgc cctggagcct    8580
cttgttttag agacccttcc cagcagctcc tggcatctag gtagtgcagt gacatcatgg    8640
agtgttcggg aggtggccag tgcctgaagc ccacaccgga ccctcttctg ccttgcaggt    8700
tgcctgcgga cacgctgggc ctctgtcctg atgctgctga gctccctggt gtctctcgct    8760
ggttctgtct acctggcctg gatcctgttc ttcgtgctct atgatttctg cattgttgt     8820
atcaccacct atgctatcaa cgtgagcctg atgtggctca gtttccggaa ggtccaagaa    8880
ccccagggca aggctaagag gcactgagcc ctcaacccaa gccaggctga cctcatctgc    8940
tttgctttgg catgtgagcc ttgcctaagg gggcatatct gggtccctag aaggccctag    9000
atgtgggct tctagattac cccctcctcc tgccatacct gcacatgaca atggaccaaa     9060
tgtgccacac gctcgctctt ttttacaccc agtgcctctg actctgtccc catgggctgg    9120
tctccaaagc tctttccatt gcccaggag ggaaggttct gagcaataaa gtttcttaga    9180
tcaatcagcc aagtctgaac catgtgtctg ccatggactg tggtgctggg cctccctcgg    9240
```

```
tgttgccttc tctggagctg ggaagggtga gtcagaggga gagtggaggg cctgctggga    9300
agggtggtta tgggtagtct catctccagt gtgtggagtc agcaaggcct ggggcaccat    9360
tggcccccac ccccaggaaa caggctggca gctcgctcct gctgcccaca ggagccaggc    9420
ctcctctcct gggaaggctg agcacacacc tggaagggca ggctgcccct ctggttctgt    9480
aaatgcttgc tgggaagttc ttccttgagt ttaactttaa cccctccagt tgccttatcg    9540
accattccaa gccagtattg gtagccttgg agggtcaggg ccaggttgtg aaggttttg     9600 ttttgcctat tatgccctga ccacttacct acatgccaag cactgtttaa gaacttgtgt    9660
tggcagggtg cagtggctca cacctgtaat ccctgtactt ggaggcca aggcaggagg     9720 atcacttgag gccaggagtt ccagaccagc ctgggcaaaa tagtgagacc cctgtctcta    9780
caaaaaaaaa aaaaaaaaaa aattagccag catggtggt gtatgtacct atagtcccaa    9840
ctaatcggga agctggcggg aagactgctt gagcccagaa ggttgaggct gcagtgagcc    9900
atgatcactg cactccagcc tgagcaacag agcaagaccg tctccaaaaa aaaacaaaaa    9960
acaaaaaaaa acttgtgtta acgtgttaaa ctcgtttaat ctttacagtg atttatgagg   10020
tgggtactat tattatccct atcttgatga tagggacaga gtggctaatt agtatgcctg   10080
agatcacaca gctactgcag gaggctctca ggatttgaat ccacctggtc catctggctc   10140
cagcatctat atgcttttt ttttgttggt ttgttttga gacggacttt cgctcttgtt    10200
gtccaggctg gagtgcaatg gcacaatttc ggctcaccac aacctccacc tcccaggttc   10260
aagtgattct cctgcctcag cctcccgagt agctgggatt acaggcatgc gccaccaggc   10320
ctggctaatt ttgtattttt agtagagaca gtgtttctct atgttggtca ggctggtctc   10380
gcactcccga cctcaggtga tctgcctgct ttggcctccc aaagtgctgg gattacaggc   10440
gtgagccacc atgcccggcc agcatctata atatatgcta aaccttaccc acagctgcct   10500 ctgtctggg gtcaggttc ttgaatggtc tgggccagcc tgagttagga gtgggaagag    10560
gaagaggagg cacgcgccaa agtgttcttc ccgcctgacc gagtcctctg cgcctatgag   10620
gaaggtgggc accgctgtca ccctgttcc caggaagcca gcaggccag ggagatactg    10680 ggatttgcca aaggctcaca gcgagcaagc agcagtgggt gctggctcct caccactcag   10740
cctggcacac actgtctctg agcagacctg ggagaaggca tgtgaaaccc acctagccct   10800
ggctggaaga gaagtggggg agtggaaatg aaaagtgggg actgggagga gctgcccacg   10860
tgccctccat ggttccagga tggcactttc atgctgggag tgagcttgcc ctgtgccagg   10920
ctgtcattga gacgttttcc attcaacaac tgtttctcag acaaggcaca ggcaggttag   10980
ctctcccagg ccactcaagt agtaaggaaa cagatttaaa cccagacaat ttggctccac   11040
ggctaaggcc cagagagggg tggtgacaag cctagggtca cacagccaca gcccagagc    11100 taggaactgc tggctagggc aagcagacag ctgaatccta gccaactgga ggtggagcag   11160
aggtggagcc agggagaccc aggtggcctc                                    11190
```

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
tcttggagtg aggaaggcaa t                                              21

<210> SEQ ID NO 3

```
<211> LENGTH: 20
<212> TYPE: DNA
<213> ORGANISM: Artificial Sequence
<220> FEATURE:
<223> OTHER INFORMATION: Synthetic

<400> SEQUENCE: 3
gacaggtctg gacaacgtgg                                              20

<210> SEQ ID NO 4
<211> LENGTH: 13
<212> TYPE: DNA
<213> ORGANISM: Artificial Sequence
<220> FEATURE:
<223> OTHER INFORMATION: Synthetic

<400> SEQUENCE: 4
ctcaggtgat cca                                                     13

<210> SEQ ID NO 5
<211> LENGTH: 25
<212> TYPE: DNA
<213> ORGANISM: Artificial Sequence
<220> FEATURE:
<223> OTHER INFORMATION: Synthetic

<400> SEQUENCE: 5
ggatgccaga tgattattct ggagt                                        25

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
tcattatgct aacgcctggc c                                            21

<210> SEQ ID NO 7
<211> LENGTH: 14
<212> TYPE: DNA
<213> ORGANISM: Artificial Sequence
<220> FEATURE:
<223> OTHER INFORMATION: Synthetic

<400> SEQUENCE: 7
caacaccccc cttc                                                    14

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
cttggtgatc cacacagctg a                                            21

<210> SEQ ID NO 9
<211> LENGTH: 26
<212> TYPE: DNA
<213> ORGANISM: Artificial Sequence
<220> FEATURE:
<223> OTHER INFORMATION: Synthetic

<400> SEQUENCE: 9
```

```
aaaagactcc tgttagttac ctcccc                                              26
```

```
<210> SEQ ID NO 10
<211> LENGTH: 17
<212> TYPE: DNA
<213> ORGANISM: Artificial Sequence
<220> FEATURE:
<223> OTHER INFORMATION: Synthetic

<400> SEQUENCE: 10
agctagctgc tcatcac                                                        17
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
taccccctcc tcctgccata                                                     20
```

```
<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
ccagcaggcc ctccactc                                                       18
```

```
<210> SEQ ID NO 13
<211> LENGTH: 15
<212> TYPE: DNA
<213> ORGANISM: Artificial Sequence
<220> FEATURE:
<223> OTHER INFORMATION: Synthetic

<400> SEQUENCE: 13
tcctcctgcc atacc                                                          15
```

```
<210> SEQ ID NO 14
<211> LENGTH: 10
<212> TYPE: DNA
<213> ORGANISM: Homo sapiens

<400> SEQUENCE: 14
ccgatctctg                                                                10
```

```
<210> SEQ ID NO 15
<211> LENGTH: 10
<212> TYPE: DNA
<213> ORGANISM: Homo sapiens

<400> SEQUENCE: 15
ccgagctctg                                                                10
```

```
<210> SEQ ID NO 16
<211> LENGTH: 10
<212> TYPE: DNA
<213> ORGANISM: Homo sapiens
```

-continued

```
<400> SEQUENCE: 16
tcggtccgca                                                              10

<210> SEQ ID NO 17
<211> LENGTH: 10
<212> TYPE: DNA
<213> ORGANISM: Homo sapiens

<400> SEQUENCE: 17
taggtccgca                                                              10

<210> SEQ ID NO 18
<211> LENGTH: 10
<212> TYPE: DNA
<213> ORGANISM: Homo sapiens

<400> SEQUENCE: 18
tacgttcgcg                                                              10

<210> SEQ ID NO 19
<211> LENGTH: 10
<212> TYPE: DNA
<213> ORGANISM: Homo sapiens

<400> SEQUENCE: 19
ccggtccccg                                                              10

<210> SEQ ID NO 20
<211> LENGTH: 10
<212> TYPE: DNA
<213> ORGANISM: Homo sapiens

<400> SEQUENCE: 20
ccggtccgtg                                                              10

<210> SEQ ID NO 21
<211> LENGTH: 10
<212> TYPE: DNA
<213> ORGANISM: Homo sapiens

<400> SEQUENCE: 21
tcgagctctg                                                              10

<210> SEQ ID NO 22
<211> LENGTH: 10
<212> TYPE: DNA
<213> ORGANISM: Homo sapiens

<400> SEQUENCE: 22
tcggtccgcg                                                              10
```